(12) United States Patent
Tobinick

(10) Patent No.: US 6,419,934 B1
(45) Date of Patent: *Jul. 16, 2002

(54) TNF MODULATORS FOR TREATING NEUROLOGICAL DISORDERS ASSOCIATED WITH VIRAL INFECTION

(76) Inventor: Edward L. Tobinick, 100 UCLA Medical Plz., Suite 205, Los Angeles, CA (US) 90024-6903

( * ) Notice: Subject to any disclaimer, the term of this patent is extended or adjusted under 35 U.S.C. 154(b) by 0 days.

This patent is subject to a terminal disclaimer.

(21) Appl. No.: 09/654,996

(22) Filed: Sep. 5, 2000

Related U.S. Application Data

(63) Continuation-in-part of application No. 09/563,651, filed on May 2, 2000, which is a continuation-in-part of application No. 09/476,643, filed on Dec. 31, 1999, now Pat. No. 6,177,077, which is a continuation-in-part of application No. 09/275,070, filed on Mar. 23, 1999, now Pat. No. 6,015,557, which is a continuation-in-part of application No. 09/256,388, filed on Feb. 24, 1999, now abandoned.

(51) Int. Cl.⁷ ............................................. A61K 9/00
(52) U.S. Cl. ..................... 424/400; 424/422; 424/427; 424/434; 424/134.1; 514/885; 514/898; 514/362; 514/363; 514/364
(58) Field of Search ................. 514/362, 363, 514/364, 400, 898, 885; 424/134.1, 422, 427, 434

(56) References Cited

U.S. PATENT DOCUMENTS

| | | | |
|---|---|---|---|
| 4,199,574 A | | 4/1980 | Schaeffer |
| 5,559,114 A | | 9/1996 | Exley |
| 5,574,022 A | | 11/1996 | Roberts et al. |
| 5,602,157 A | * | 2/1997 | Christensen, IV .......... 514/362 |
| 5,605,690 A | | 2/1997 | Jacobs et al. |
| 5,650,396 A | | 7/1997 | Carlino et al. |
| 5,656,272 A | | 8/1997 | Le et al. |
| 5,756,482 A | | 5/1998 | Roberts et al. |
| 5,866,581 A | | 2/1999 | Boon |
| 6,001,828 A | * | 12/1999 | Andrulius Jr. et al. ...... 514/221 |
| 6,093,819 A | | 7/2000 | Hanson |
| 6,180,355 B1 | * | 1/2001 | Alexander et al. ........... 435/7.1 |

\* cited by examiner

*Primary Examiner*—Thurman K. Page
*Assistant Examiner*—Lakshni Channavajjala
(74) *Attorney, Agent, or Firm*—Ezra Sutton PA

(57) ABSTRACT

A method for inhibiting the action of TNF for treating neurological conditions in a human by administering a TNF antagonist for reducing the inflammation of neuronal tissue of said human, or for modulating the immune response affecting neuronal tissue of said human, comprising the step of:

administering a therapeutically effective dosage level to said human of said TNF antagonist selected from the group consisting of etanercept, infliximab, and D2E7 (a human anti-TNF mAb from Knoll Pharmaceuticals) for reducing the inflammation of neuronal tissue of said human, or for modulating the immune response affecting neuronal tissue of said human.

In addition, for the viral-associated neurological disorders, the following additional step is performed:

administering a therapeutically effective dosage level to said human of an antiviral agent or anti-retroviral agents for reducing the inflammation of neuronal tissue of said human, or for modulating the immune response affecting neuronal tissue of said human.

84 Claims, No Drawings

TNF MODULATORS FOR TREATING NEUROLOGICAL DISORDERS ASSOCIATED WITH VIRAL INFECTION

RELATED APPLICATIONS

This is a continuation-in-part of application Ser. No. 09/563,651, filed on May 2, 2000, which is a continuation-in-part of application Ser. No. 09/476,643, filed on Dec. 31, 1999, now U.S. Pat. No. 6,177,077, which is a continuation-in-part of application Ser. No. 09/275,070, filed on Mar. 23, 1999, now U.S. Pat. No. 6,015,557, which is a continuation-in-part of application Ser. No. 09/256,388, filed on Feb. 24, 1999, now abandoned.

FIELD OF THE INVENTION

TNF modulation is established as a new treatment modality for rheumatoid arthritis and Crohn's Disease. TNF antagonists for the treatment of neurological disorders are the subject of two previous patents by the inventor. The present invention discloses new clinical data and concepts related to treating neurological damage associated with viral infection, epilepsy, and stroke.

BACKGROUND OF THE INVENTION

Tumor necrosis factor (TNF) is intimately involved in the nervous system. It is central to the response to injury, either virally induced, or occurring as a result of mechanical trauma. TNF is also central to neuronal apoptosis, a process important in many neurological disorders.

TNF, a naturally occurring cytokine, plays a key role in the inflammatory response, in the immune response, and in the response to infection. TNF is formed by the cleavage of a precursor transmembrane protein, forming soluble molecules which aggregate in vivo to form trimolecular complexes. These complexes then bind to receptors found on a variety of cells. Binding produces an array of pro-inflammatory effects, including release of other pro-inflammatory cytokines, including IL-6, IL-8, and IL-1; release of matrix metalloproteinases; and up regulation of the expression of endothelial adhesion molecules, further amplifying the inflammatory and immune cascade by attracting leukocytes into extravascular tissues.

Specific inhibitors of TNF, only recently commercially available, now provide the possibility of therapeutic intervention in TNF mediated disorders. These antagonists, mainly developed to treat rheumatoid arthritis, include etanercept (Enbrel (R)—Immunex Corporation); infliximab (Rhemicade (R)—Johnson and Johnson); and D2E7, a human anti-TNF monoclonal antibody (Knoll Pharmaceuticals). These agents appear to be generally safe for chronic administration, and their efficacy for the treatment of rheumatoid arthritis has been established.

Few effective therapeutic agents are available for the treatment of neurological disorders. The nervous system has only a limited capacity for repair. Neurological injury is therefore often permanent, irreversible, and clinically devastating. There is an urgent need for effective treatments for a wide variety of neurological conditions, many of which are chronic, progressive, and incurable. TNF modulation with these new agents offers a new modality of treatment for many of these disorders.

TNF MODULATION FOR VIRAL-INDUCED NEUROLOGICAL DISORDERS

Viral infections are associated with a wide variety of neurological disorders. These include Viral Meningitis, Viral Encephalitis, Postherpetic Neuralgia, HIV-associated Neurological Disorders (including HIV Dementia, HIV-associated Myelopathy, and HIV-associated Peripheral Neuropathy), HTLV-1 Myelopathy, Poliomyelitis, Influenza, Reye's Syndrome, Meniere's Disease, Trigeminal Neuralgia, and Herpes Zoster. Additionally, several neurological disorders of unknown etiology are probably the result of "cryptogenic" viral infection.

Neurological damage associated with viral infection can occur closely in association with the initial infection, or can, in other cases, follow after an extended interval. This damage occurring after a long interval can be associated with reactivation of a latent viral infection, as with herpes zoster, or through other mechanisms, not yet fully elucidated, such as in postpolio syndrome. Whether occurring acutely or after a long interval, TNF is centrally involved.

The response to viral infection causes immune system activation. Neurological damage associated with viral infection can be caused directly by viral invasion, or secondarily by immune activation. TNF modulation can limit this damage. TNF modulators can therefore be used to treat the above viral-associated disorders, either alone or in combination with antiviral therapy.

TNF MODULATORS AND ANTIVIRAL MEDICATIONS

The object of the present invention is to provide clinical benefit to patients who have, or are at risk of experiencing a neurological disorder, through the use of a TNF modulator (the term modulator is used here synonymously with antagonist), either alone or in combination with an antiviral medication. TNF modulation in many of the disorders discussed will be effective as monotherapy. In the disorders discussed in which neurological damage occurs in association with active viral replication, such as with Herpes Zoster, or with Influenza infection, the use of additional antiviral therapy in combination with TNF modulation will provide additive, or even synergistic benefit. Monotherapy with the antiviral agents mentioned is not considered adequate therapy for any of the neurological conditions discussed. In some instances, monotherapy with a TNF antagonist will be effective, and the addition of an antiviral medication will produce added benefit. In other cases, TNF monotherapy will be ineffective, as will antiviral therapy by itself, but combination therapy will produce clinical improvement.

Combination therapy can be beneficial through several mechanisms, including the following:

1. Certain TNF modulators may be themselves directly viricidal or may directly inhibit viral growth or replication.
2. TNF may itself be a growth factor for certain viruses. TNF antagonism would, in these situations, function directly as an additional antiviral agent. This may be related to the research that has demonstrated that TNF is a growth factor for certain tumors, such as ovarian carcinoma.
3. In certain instances, TNF antagonism will have no direct effect on viral growth but will instead produce clinical improvement through direct modulation of the immune response which is associated with an active viral infection, or which was initiated by a preceding viral infection.

DESCRIPTION OF THE PRIOR ART

Pharmacologic chemical substances, compounds, and agents which are used for the treatment of neurological disorders, trauma, injuries, and compression having various organic structures and metabolic functions have been disclosed in the prior art. For example, U.S. Pat. Nos. 5,756,482 and 5,574,022 to Roberts et al disclose methods of attenuating physical damage to the nervous system and to the spinal cord after injury using steroid hormones or steroid precursors, such as pregnenolone and pregnenolone sulfate in conjunction with a non-steroidal anti-inflammatory substance, such as indomethacin. These prior art patents do not teach the use of the TNF modulators discussed herein for the suppression and inhibition of the action of TNF in the human body to treat the neurological disorders of the present invention.

U.S. Pat. No. 5,605,690 to Jacobs discloses a method for treating TNF-dependent inflammatory diseases, such as arthritis, by administering a TNF antagonist, such as soluble human TNFR (a sequence of amino acids), to a human. This prior art patent does not teach the use of the TNF modulators discussed herein for the suppression and inhibition of the action of TNF in the human body to treat the neurological disorders of the present invention.

U.S. Pat. No. 5,656,272 to Le et al discloses methods of treating TNF-alpha-mediated Crohn's disease using chimeric anti-TNF antibodies. This prior art patent does not teach the use of the TNF modulators discussed herein for the suppression and inhibition of the action of TNF in the human body to treat the neurological disorders of the present invention.

U.S. Pat. No. 5,650,396 discloses a method of treating multiple sclerosis (MS) by blocking and inhibiting the action of TNF in a patient. This prior art patent does not teach the use of the TNF modulators discussed herein for the suppression and inhibition of the action of TNF in the human body to treat the neurological disorders of the present invention.

U.S. Pat. No. 6,093,819 to Hanson discusses the preparation of Famciclovir. This prior art patent does not teach the use of the TNF modulators discussed herein for the suppression and inhibition of the action of TNF in the human body or the use of Famciclovir or Acyclovir to treat the neurological disorders of the present invention.

U.S. Pat. No. 5,559,114 to Exley discloses the use of Acyclovir and Famciclovir at higher than normal doses to treat autoimmune disease. This prior art patent does not teach the use of the TNF modulators discussed herein for the suppression and inhibition of the action of TNF in the human body or the use of Famciclovir or Acyclovir to treat the neurological disorders of the present invention.

U.S. Pat. No. 4,199,574 to Schaefer discloses methods to treat viral infections. This prior art patent does not teach the use of the TNF modulators discussed herein for the suppression and inhibition of the action of TNF in the human body or the use of Famciclovir or Acyclovir to treat the neurological disorders of the present invention.

U.S. Pat. No. 5,866,581 to Boon discloses the use of Penciclovir and Famciclovir for the treatment or prophylaxis of Postherpetic Neuralgia. These drugs, however, are not effective for this use when used alone. This prior art patent does not teach the use of the combination of a TNF modulator together with Penciclovir or Famciclovir to treat the neurological disorders of the present invention. Such a combination is necessary to be effective in the treatment or prophylaxis of Postherpetic Neuralgia.

OBJECTS OF THE INVENTION

Accordingly, it is an object of the present invention to provide TNF modulation for treating neurological disorders associated with viral infection, including Postherpetic Neuralgia (PHN), Viral Meningitis, Viral Encephalitis, Poliomyelitis, HIV, HTLV-1 Myelopathy, Reye's Syndrome, Meniere's Disease, Trigeminal Neuralgia, Influenza, and Herpes Zoster.

It is a further object of the present invention to treat neurological disorders associated with viral infection with a combination therapy of TNF modulators and antiviral agents or antiretroviral agents. These disorders include PHN, Influenza, HIV, Herpes Zoster, and others.

It is a further object of the present invention to treat epileptic disorders with TNF modulators alone or with antiseizure drugs.

It is a further object of the present invention to treat stroke and cerebrovascular disease with TNF modulators.

It is a further object of the present invention to use TNF modulators as neuroprotective agents for patients who have had a previous stroke to limit future stroke damage, or for patients who have a cerebrovascular disease to limit the damage from future occlusive events.

SUMMARY OF THE INVENTION

The present invention provides a method for inhibiting the action of TNF for treating neurological conditions in a human by administering a TNF antagonist for reducing the inflammation of neuronal tissue of said human, or for modulating the immune response affecting neuronal tissue of said human, comprising the step of:

administering a therapeutically effective dosage level to said human of said TNF antagonist selected from the group consisting of etanercept, infliximab, and D2E7 (a human anti-TNF mAb from Knoll Pharmaceuticals) for reducing the inflammation of neuronal tissue of said human, or for modulating the immune response affecting neuronal tissue of said human.

In addition, for the viral-associated neurological disorders, the following additional step is performed:

administering a therapeutically effective dosage level to said human of an antiviral agent or anti-retroviral agents for reducing the inflammation of neuronal tissue of said human, or for modulating the immune response affecting neuronal tissue of said human.

DESCRIPTION OF THE PREFERRED EMBODIMENTS

The disorders described herein may be treated with one or more of the following treatment regimens:

TREATMENT REGIMENS

Acute.
Acute Monotherapy (AM).
Acute Combination Therapy (AC).
Chronic.
Chronic Monotherapy (CM).
Chronic Combination Therapy (CC).
Cerebrospinal Fluid (CSF).
Group 1: Acute Regimens This group of regimens is generally used for clinical disorders of short duration, or for those in which chronic therapy is unlikely to lead to additional benefit. Methods of administration for the TNF modulator include the subcutaneous, intravenous, and intramuscular routes. Antiviral medication routes of administration include oral or intravenous. Duration of administration is 30 days or less. The two subsets of this group are:

1. Acute Monotherapy (AM): This consists of treatment with a TNF modulator without the addition of an antiviral agent.
2. Acute Combination Therapy (AC): This consists of treatment with a TNF modulator and concomitant administration of an antiviral agent.

Group 2: Chronic Regimens

This group of regimens is used for clinical disorders which are chronic, and for which chronic administration of a TNF modulator will lead to continuing benefit. Methods of administration for the TNF modulator include the subcutaneous, intravenous, and intramuscular routes. Antiviral medications in these regimens are oral. Duration of therapy is greater than 30 days, and may be lifelong with selected chronic disorders. The two subsets of this group are:

1. Chronic Monotherapy (CM): This consists of treatment with a TNF modulator without the addition of an antiviral agent.
2. Chronic Combination Therapy (CC): This consists of treatment with a TNF modulator and concomitant administration of an antiviral agent.

Group 3: CSF Regimens (CSF)

This group of regimens is used for serious, generally life-threatening disorders. Routes of administration include intrathecal and/or intracerebroventricular administration into the cerebrospinal fluid (CSF). Duration of treatment can be either acute or chronic.

MODIFICATION OF MONOTHERAPY REGIMENS

There is one important additional factor to consider regarding the above monotherapy regimens. Future research may reveal the association of presently undiscovered microbial agents (including viruses, bacteria, prions, chlamydia, etc.) with the neurological disorders discussed herein. Similarly, future research may also discover new antiviral agents effective for the disorders discussed herein. When this happens, the monotherapy regimens, consisting of a TNF modulator alone, are designed so as to allow the addition of these new antimicrobial agents or new antiviral agents as concomitant therapy. The TNF modulators discussed herein have no known drug interactions, and are ideal for combination therapy with a variety of different agents.

DISORDERS

The disorders described herein may be treated with one or more of the treatment regimens discussed above. Listed below are each of the disorders, as well as the codes for the appropriate treatment regimens.

1. Chronic Epileptic Disorders, including, but not limited to:
   Petit Mal Epilepsy.
   Temporal Lobe Epilepsy.
   Post-Traumatic Epilepsy.
   Generalized Seizure Disorder.
   (CM) for all forms of Epilepsy.
2. Postherpetic Neuralgia (AM, AC, CM, CC).
3. Viral Meningitis (AC).
4. Viral Encephalitis (AC).
5. Poliomyelitis-associated neurological disorders:
   Acute Poliomyelitis (AM, AC).
   Postpolio Syndrome (CM).
6. HIV-Associated Neurological Disorders, including:
   HIV Dementia (CSF, CC).
   HIV-associated Myelopathy (AC, CSF, CC).
   HIV-associated Peripheral Neuropathy (CC).
7. HTLV-1 Myelopathy (CC).
8. Influenza (AC).
9. Trigeminal Neuralgia (AM, AC, CM, CC).
10. Reyets Syndrome (AM).
11. Meniere's Disease (CM).
12. Reflex Sympathetic Dystrophy (CM).
13. Cerebrovascular Disease (CM).
14. Prophylaxis of Brain Injury caused by Stroke (CM).
15. Chronic Inflammatory Demyelinating Polyneuropathy (CM).

TNF MODULATION FOR THE TREATMENT OF POSTHERPETIC NEURALGIA (PHN)

Herpes Zoster (Zoster) is a dermatomal cutaneous bullous eruption due to reactivation of varicella-zoster virus which has remained latent in the dorsal root ganglion and sensory nerves. It is frequently accompanied by severe pain due to neurologic damage which occurs as a result of viral replication and the ensuing immune response. Approximately 300,000 new cases occur each year in the United States. Pain associated with Zoster can precede, occur simultaneously, or follow the appearance of the rash. Patients are considered to have Postherpetic Neuralgia (PHN) if the pain following Zoster persists for greater than one month following healing of the cutaneous eruption. After age 70, PHN occurs in 73% of patients who develop Zoster. Pain lasting more than one year occurs in 48% of patients with PHN over age 70. Pathological changes which have been documented after Zoster can include inflammation, hemorrhagic necrosis, and neuronal loss in the dorsal root ganglion; demyelination, wallerian degeneration, and sclerosis of peripheral nerves; acute degeneration of the dorsal horn of the spinal cord, and rarely, unilateral segmental myelitis and leptomeningitis.

Because of the central role of TNF in the pathogenesis of neuronal damage in PHN, a clinical trial of a TNF modulator combined with an antiviral agent was conducted by the inventor for the treatment of established Postherpetic Neuralgia. Patients were treated with a combination therapy consisting of etanercept, 25 mg subcutaneously administered twice per week, and Famciclovir given orally twice a day. A sustained clinical response resulting in pain relief was seen, generally within two weeks of initiating therapy. These results are in stark contrast to previous trials of drug therapy for treatment of PHN, which have generally been disappointing. Relief of Postherpetic Neuralgia with antiviral agents alone has not been demonstrated.

The trial conducted by the inventor was for patients with established PHN. Neuronal damage, however, can occur even prior to the onset of the skin rash of Zoster, as evidenced by patients whose pain preceded the cutaneous eruption. TNF modulation is therefore most effective if administered at the time of diagnosis of Zoster. TNF modulation thereby limits neurologic damage and prevents the occurrence of PHN if administered early.

TNF MODULATION FOR CHRONIC EPILEPTIC DISORDERS

Epilepsy affects 2.3 million Americans. Currently, drug treatment regimens are limited by drug side effects and incomplete efficacy. The major forms of epilepsy include Generalized Seizure Disorder (Grand Mal Type), Petit Mal Epilepsy, Temporal Lobe Epilepsy, and Post-Traumatic Epilepsy, as well as less common forms. Many of these disorders begin with an inflammatory focus in the brain. Treatment of these individuals with a TNF modulator will ameliorate this inflammation, resulting in clinical improvement. The addition of TNF modulation to an antiseizure drug regimen will result in diminution of seizure activity. Monotherapy with a TNF modulator may also be successful, and may result in continual improvement over time, with eventual elimination of active inflammation.

COMBINATION THERAPY FOR INFLUENZA

Influenza merits additional discussion. Influenza is not conventionally thought of as a neurological disease. Nevertheless, there is neurological involvement during the acute febrile phase, as evidenced by headache, lethargy, fatigue, and eye pain with movement. TNF modulation combined with specific Influenza antiviral therapy, such as with oseltamivir phosphate, results in additional clinical improvement over that seen with oseltamivir alone. Also, TNF modulation alone provides improvement.

COMBINATION THERAPY FOR VIRAL-ASSOCIATED NEUROLOGICAL DISORDERS

Other examples of combination therapy include TNF modulation plus antiretroviral therapy for treatment of HIV-associated Neurological Disorders (including HIV Dementia, HIV-associated Myelopathy, and HIV-associated Peripheral Neuropathy); and TNF modulation plus intravenous Acyclovir for treatment of Herpes Encephalitis. Other forms of Viral Encephalitis or Viral Meningitis will also benefit from combination therapy when antiviral agents effective for the causative virus are available. TNF modulation alone will benefit other forms of viral central nervous system infection or other virally-induced disorders, such as Reye's Syndrome.

VIRAL MENINGITIS AND VIRAL ENCEPHALITIS

Active viral infection of the leptomeninges (viral meningitis) or the brain parenchyma (viral encephalitis) can be caused by many different viruses, and are relatively common (greater than 10 per 100,000 person years). These infections are generally acute, and neurologic symptoms include headache, photophobia, stiff neck, and when encephalitis occurs, alteration of attention or consciousness. Effective antiviral therapy is available against Herpes Simplex virus, CMV, and Varicella. TNF modulation is indicated as monotherapy or as combination therapy when specific antiviral therapy is available.

ACUTE POLIOMYELITIS

Neurologic involvement follows enteric infection with the poliovirus, which is both myotropic and neurotropic. During infection, motor neurons of the spinal cord and brain stem are selectively destroyed, resulting in weakness or paralysis. No specific treatment is available for the acute infection, but TNF is centrally involved, and TNF modulation, as monotherapy, results in clinical improvement and limitation of neurological damage.

POSTPOLIO SYNDROME

Gradually progressive weakness occurring many years after the initial episode of poliomyelitis is characteristic of this previously-untreatable syndrome. TNF is centrally involved in the processes of inflammation and apoptosis involving both nerve and muscle. TNF modulator therapy, on a chronic basis, is the treatment of choice.

HIV DEMENTIA

Neurologic disease occurs in the majority of patients infected with human immunodeficiency virus (HIV). Impaired cognition, lower limb weakness, and poor balance are among the many signs of this disorder. There is evidence that HIV infection of the brain results in cytokine release from brain microglial cells, resulting in inflammation and apoptosis of brain cells. TNF modulation, in combination with antiretroviral therapy, decreases neurological damage, thereby slowing progression of this serious disorder. Certain patients will benefit from delivery of the TNF modulator directly into the cerebrospinal fluid on a chronic basis. This may be achieved with an implantable pump, as is done with chronic baclofen therapy. Other patients may be treated with chronic subcutaneous or intermittent intravenous TNF modulator therapy.

HIV-ASSOCIATED MYELOPATHY

Characterized by a slowly-progressive gait disturbance in patients with HIV in which other spinal cord diseases have been ruled out, this disorder is not adequately treated by antiretroviral therapy alone. Nevertheless, the combination of TNF modulation and aggressive antiretroviral therapy chronically slows disease progression. Routes of administration are the same as in HIV Dementia.

HIV-ASSOCIATED PERIPHERAL NEUROPATHY

Peripheral nerve damage in patients with HIV disease is common and can result in a myriad of signs and symptoms. TNF modulation on a chronic basis is beneficial, combined with antiretroviral therapy. Routs of administration are subcutaneous or intermittent intravenous delivery of the TNF modulator.

HTLV-1 MYELOPATHY

Formerly known as Tropical Spastic Paraparesis, and also called HAM (for HTLV-1 associated Myelopathy), this disorder, caused by infection with Human T-Lymphotropic Virus type 1, causes progressive weakness of the lower extremities. Antiretroviral therapy has been of limited value, but systemic steroids have been somewhat effective. TNF modulator therapy on a chronic basis, either alone or in combination with antiretroviral therapy, is indicated.

TRIGEMINAL NEURALGIA

Episodic facial pain in the distribution of one of the branches of the trigeminal nerve, also known as tic douloureux, is an uncommon, yet disabling disorder of older patients. TNF modulator therapy is indicated to reduce pain and inflammation of this fifth cranial nerve.

REYE'S SYNDROME

This acute illness of children usually follows an acute viral infection. Brain edema, increased intracranial pressure, and fatty infiltration of the liver occur. TNF modulator therapy is indicated.

MENIERE'S DISEASE

Meniere's Disease, also called Meniere's Syndrome, is characterized by episodic vertigo, tinnitus, and progressive hearing loss. TNF is central to the pathology involving the endolymphatic sac, the cochlea, and associated nerve cells. TNF modulator therapy, on a chronic basis, is indicated.

REFLEX SYMPATHETIC DYSTROPHY

Also known as Chronic Regional Pain Syndrome (CRPS), describes a chronic pain syndrome often associated with autonomic dysfunction, edema, dystrophy, and atrophy. As in Postherpetic Neuralgia, these patients experience hyperalgesia and mechanical allodynia. TNF modulator therapy is a breakthrough new modality of treatment for these individuals because of the central role of TNF in the pathogenesis of this disorder.

MULTIPLE SCLEROSIS

TNF modulator therapy for Multiple Sclerosis has been disclosed by the inventor in his previous patents. New research has implicated the Herpesvirus family with exacerbations of MS. Combination therapy consisting of a TNF modulator along with an antiviral medication provides additional benefit as compared to antiviral therapy alone, or TNF modulator therapy alone. The antiviral medications currently available of greatest utility are Acyclovir, Famciclovir, and Valaciclovir.

CHRONIC INFLAMMATORY DEMYELINATING POLYNEUROPATHY (CIDP)

A chronic neurologic disorder is accompanied by widespread demyelination, usually evidenced by slowly-evolving weakness and sensory loss. Current treatment regimens with corticosteroids, plasmapheresis, and intravenous gamma globulin are often inadequate. Treatment regimen recommended here is Chronic Monotherapy with a TNF modulator (CM).

TNF MODULATION FOR STROKE AND CEREBROVASCULAR DISEASE

TNF is centrally involved in the brain damage caused by stroke. Much of this damage occurs acutely, within minutes or hours of the initial vascular event. TNF modulators can function as neuroprotective agents, but to be maximally effective, they must be administered acutely. Two methods of administration are thereby suggested: rapid intravenous infusion, if possible within hours of the initial event; or administration via a chronic route, prior to stroke occurrence, as a preventive regimen. Chronic administration would be indicated for individuals at increased risk of a subsequent stroke. An example of such a situation would be the administration of etanercept, 25 mg subcutaneously twice per week, to patients who have had a previous stroke. These individuals, who are at increased risk of a subsequent stroke, would thereby have a therapeutic level of etanercept circulating at all times. Etanercept would function to limit stroke damage. TNF modulation will also have a directly beneficial effect on atherosclerotic vascular disease. Atherosclerosis is accompanied by inflammation in the vessel wall. TNF modulation decreases this inflammation, thereby diminishing the rate of progression of atherosclerosis. Patients with cerebrovascular disease receive a double benefit from the use of chronic TNF modulator therapy, both through the reduction of cerebral and carotid atherosclerosis, and as a neuroprotective agent during any cerebrovascular occlusive events that do occur.

ADVANTAGES OF THE PRESENT INVENTION

Accordingly, an advantage of the present invention is that it provides TNF modulation for treating neurological disorders associated with viral infection, including Postherpetic Neuralgia (PHN), Viral Meningitis, Viral Encephalitis, Poliomyelitis, HIV, HTLV-1 Myelopathy, Reye's Syndrome, Meniere's Disease, Trigeminal Neuralgia, Influenza, and Herpes Zoster.

A further advantage of the present invention is that it provides a method to treat neurological disorders associated with viral infection with a combination therapy of TNF modulators and antiviral agents or antiretroviral agents. These disorders include PHN, Influenza, HIV, Herpes Zoster, and others.

A further advantage of the present invention is that it provides a method to treat epileptic disorders with TNF modulators alone or with antiseizure drugs.

A further advantage of the present invention is that it provides a method to treat stroke and cerebrovascular disease with TNF modulators.

A further advantage of the present invention is that it provides a method of using TNF modulators as neuroprotective agents for patients who have had a previous stroke to limit future stroke damage, or for patients who have a cerebrovascular disease to limit the damage from future occlusive events.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A method for inhibiting the action of TNF for treating neurological conditions in a human by administering a TNF antagonist for reducing the inflammation of neuronal tissue or the neuromuscular junction of said human, or for modulating the immune response affecting neuronal tissue or the neuromuscular junction of said human, comprising the step of:

a) administering a therapeutically effective dosage level to said human of said TNF antagonist selected from the group consisting of etanercept, infliximab, and D2E7 (a human anti-TNF mAb from Knoll Pharmaceuticals) for reducing the inflammation of neuronal tissue or the neuromuscular junction of said human, or for modulating the immune response affecting neuronal tissue or the neuromuscular junction of said human.

2. A method for inhibiting the action of TNF in accordance with claim 1, wherein the step of administering said TNF antagonist is performed through any of the following routes: subcutaneous, intravenous, intrathecal, intramuscular, parenteral, or intracerebroventricular.

3. A method for inhibiting the action of TNF in accordance with claim 1, wherein the step of administering said dosage level is for treating chronic epileptic disorders.

4. A method for inhibiting the action of TNF in accordance with claim 1, wherein the step of administering said dosage level is for treating Postherpetic Neuralgia.

5. A method for inhibiting the action of TNF in accordance with claim 1, wherein the step of administering said dosage level is for the prevention of Postherpetic Neuralgia.

6. A method for inhibiting the action of TNF in accordance with claim 1, wherein the step of administering said dosage level is for treating Viral Encephalitis.

7. A method for inhibiting the action of TNF in accordance with claim 1, wherein the step of administering said dosage level is for treating Viral Meningitis.

8. A method for inhibiting the action of TNF in accordance with claim 1, wherein the step of administering said dosage level is for treating neurological disorders associated with HIV, including HIV Dementia, HIV-associated Myelopathy, and HIV-associated Peripheral Neuropathy.

9. A method for inhibiting the action of TNF in accordance with claim 1, wherein the step of administering said dosage level is for treating HTLV-1 Myelopathy.

10. A method for inhibiting the action of TNF in accordance with claim 1, wherein the step of administering said dosage level is for treating Reye's Syndrome.

11. A method for inhibiting the action of TNF in accordance with claim 1, wherein the step of administering said dosage level is for treating cerebrovascular disease.

12. A method for inhibiting the action of TNF in accordance with claim 1, wherein the step of administering said dosage level is for prophylaxis of brain injury caused by stroke.

13. A method for inhibiting the action of TNF in accordance with claim 1, wherein the step of administering said dosage level is for treating Trigeminal Neuralgia.

14. A method for inhibiting the action of TNF in accordance with claim 1, wherein the step of administering said dosage level is for treating influenza.

15. A method for inhibiting the action of TNF in accordance with claim 1, wherein the step of administering said dosage level is for treating Herpes Zoster.

16. A method for inhibiting the action of TNF in accordance with claim 1, wherein the step of administering said dosage level is for treating stroke.

17. A method for inhibiting the action of TNF in accordance with claim 1, wherein the step of administering said dosage level is for treating Meniere's Disease.

18. A method for inhibiting the action of TNF in accordance with claim 1, wherein the step of administering said dosage level is for treating Reflex Sympathetic Dystrophy (RSD).

19. A method for inhibiting the action of TNF in accordance with claim 1, wherein the step of administering said dosage level is for treating Chronic Inflammatory Demyelinating Polyneuropathy (CIDP).

20. A method for inhibiting the action of TNF in accordance with claim 1, wherein the step of administering said dosage level is for treating neurological disorders associated with Poliomyelitis, including acute Poliomyelitis and post-polio syndrome.

21. A method for inhibiting the action of TNF in accordance with claim 1, wherein the step of administering said TNF antagonist in the form of etanercept is performed subcutaneously in said human wherein said dosage level is in the range of 5 mg to 50 mg for acute or chronic regimens.

22. A method for inhibiting the action of TNF in accordance with claim 1, wherein the step of administering said TNF antagonist in the form of D2E7 is performed subcutaneously in said human wherein said dosage level is in the range of 20 mg to 100 mg for acute or chronic regimens.

23. A method for inhibiting the action of TNF in accordance with claim 1, wherein the step of administering said TNF antagonist in the form of infliximab is performed subcutaneously in said human wherein said dosage level is a therapeutically effective amount.

24. A method for inhibiting the action of TNF in accordance with claim 1, wherein the step of administering said TNF antagonist in the form of etanercept is performed intramuscularly in said human wherein said dosage level is in the range of 25 mg to 100 mg.

25. A method for inhibiting the action of TNF in accordance with claim 1, wherein the step of administering said TNF antagonist in the form of infliximab is performed intravenously in said human wherein said dosage level is in the range of 2.5 mg/kg to 20 mg/kg.

26. A method for inhibiting the action of TNF in accordance with claim 1, wherein the step of administering said TNF antagonist in the form of etanercept is performed intrathecally in said human wherein said dosage level is in the range of 0.1 mg to 25 mg administered from once a day to once every 3 months.

27. A method for inhibiting the action of TNF in accordance with claim 1, wherein the step of administering said TNF antagonist in the form of infliximab is performed intrathecally in said human wherein said dosage level is in the range of 0.1 mg/kg to 5 mg/kg administered from once a week to once every 3 months.

28. A method for inhibiting the action of TNF in accordance with claim 1, wherein the step of administering said TNF antagonist in the form of D2E7 is performed intrathecally in said human wherein said dosage level is in the range of 0.1 mg to 25 mg administered from once a week to once every 3 months.

29. A method for inhibiting the action of TNF in accordance with claim 1, wherein the step of administering said TNF antagonist is performed intravenously in said human wherein said dosage level is a therapeutically effective amount.

30. A method for inhibiting the action of TNF in accordance with claim 1, wherein the step of administering said TNF antagonist in the form of etanercept is performed intracerebroventricularly in said human wherein said dosage level is in the range of 0.1 mg to 25 mg administered from once a day to once a month.

31. A method for inhibiting the action of TNF in accordance with claim 1, wherein the step of administering said TNF antagonist in the form of infliximab is performed intracerebroventricularly in said human wherein said dosage level is in the range of 0.1 mg/kg to 5 mg/kg administered from once a week to once every 3 months.

32. A method for inhibiting the action of TNF in accordance with claim 1, wherein the step of administering said TNF antagonist in the form of D2E7 is performed intracerebroventricularly in said human wherein said dosage level is in the range of 0.1 mg to 25 mg administered from once a week to once every 3 months.

33. A method for inhibiting the action of TNF for treating the neurological condition of Postherpetic Neuralgia in a human by administering a TNF antagonist for reducing the inflammation of neuronal tissue of said human, or for modulating the immune response affecting neuronal tissue of said human, comprising the steps of:
   a) administering a therapeutically effective dosage level to said human of said TNF antagonist selected from the group consisting of etanercept, infliximab, and D2E7 (a human anti-TNF mAb from Knoll Pharmaceuticals) for reducing the inflammation of neuronal tissue of said human, or for modulating the immune response affecting neuronal tissue of said human; and
   b) administering a therapeutically effective dosage level to said human of an antiviral agent selected from the group consisting of Acyclovir, Valaciclovir, and Famciclovir for reducing the inflammation of neuronal tissue of said human, or for modulating the immune response affecting neuronal tissue of said human.

34. A method for inhibiting the action of TNF in accordance with claim 33, wherein the step of administering said TNF antagonist in the form of etanercept is performed subcutaneously in said human wherein said dosage level is in the range of 5 mg to 50 mg for acute or chronic regimens.

35. A method for inhibiting the action of TNF in accordance with claim 33, wherein the step of administering said TNF antagonist in the form of D2E7 is performed subcutaneously in said human wherein said dosage level is in the range of 20 mg to 100 mg for acute or chronic regimens.

36. A method for inhibiting the action of TNF in accordance with claim 33, wherein the step of administering said TNF antagonist in the form of infliximab is performed subcutaneously in said human wherein said dosage level is a therapeutically effective amount.

37. A method for inhibiting the action of TNF in accordance with claim 33, wherein the step of administering said TNF antagonist in the form of infliximab is performed intravenously in said human wherein said dosage level is in the range of 2.5 mg/kg to 20 mg/kg.

38. A method for inhibiting the action of TNF in accordance with claim 33, wherein the step of administering said TNF antagonist is performed subcutaneously in said human wherein said dosage level is a therapeutically effective amount.

39. A method for inhibiting the action of TNF in accordance with claim 33, wherein the step of administering said TNF antagonist is performed intravenously in said human wherein said dosage level is a therapeutically effective amount.

40. A method for inhibiting the action of TNF in accordance with claim 33, wherein the step of administering said antiviral agent in the form of Acyclovir is performed orally in said human, wherein said dosage level is 400 mg taken 2 to 5 times per day.

41. A method for inhibiting the action of TNF in accordance with claim 33, wherein the step of administering said antiviral agent in the form of Valaciclovir is performed orally in said human, wherein said dosage level is one gram taken once or twice per day.

42. A method for inhibiting the action of TNF in accordance with claim 33, wherein the step of administering said antiviral agent in the form of Famciclovir is performed orally in said human, wherein said dosage level is 250 mg to 500 mg taken 2 to 3 times per day.

43. A method for inhibiting the action of TNF for treating the neurological effects of influenza in a human by administering a TNF antagonist for reducing the inflammation of neuronal tissue or the neuromuscular junction of said human, or for modulating the immune response affecting neuronal tissue or the neuromuscular junction of said human, comprising the steps of:
   a) administering a therapeutically effective dosage level to said human of said TNF antagonist selected from the group consisting of etanercept, infliximab, and D2E7 (a human anti-TNF mAb from Knoll Pharmaceuticals) for reducing the inflammation of neuronal tissue or the neuromuscular junction of said human, or for modulating the immune response affecting neuronal tissue or the neuromuscular junction of said human; and
   b) administering a therapeutically effective dosage level to said human of the antiviral agent oseltamivir phosphate for reducing the inflammation of neuronal tissue or the neuromuscular junction of said human, or for modulating the immune response affecting neuronal tissue or the neuromuscular junction of said human.

44. A method for inhibiting the action of TNF in accordance with claim 43, wherein the step of administering said TNF antagonist in the form of etanercept is performed subcutaneously in said human wherein said dosage level is in the range of 5 mg to 50 mg for acute or chronic regimens.

45. A method for inhibiting the action of TNF in accordance with claim 43, wherein the step of administering said TNF antagonist in the form of D2E7 is performed subcutaneously in said human wherein said dosage level is in the range of 20 mg to 100 mg for acute or chronic regimens.

46. A method for inhibiting the action of TNF in accordance with claim 43, wherein the step of administering said TNF antagonist in the form of infliximab is performed subcutaneously in said human wherein said dosage level is a therapeutically effective amount.

47. A method for inhibiting the action of TNF in accordance with claim 43, wherein the step of administering said TNF antagonist is performed subcutaneously in said human wherein said dosage level is a therapeutically effective amount.

48. A method for inhibiting the action of TNF in accordance with claim 43, wherein the step of administering oseltamivir is performed orally in said human, wherein said dosage level is 75 mg taken 2 times per day for 5 to 10 days.

49. A method for inhibiting the action of TNF for treating neurological conditions associated with HIV in a human by administering a TNF antagonist for reducing the inflammation of neuronal tissue or the neuromuscular junction of said human, or for modulating the immune response affecting neuronal tissue or the neuromuscular junction of said human, comprising the steps of:
   a) administering a therapeutically effective dosage level to said human of said TNF antagonist selected from the group consisting of etanercept, infliximab, and D2E7 (a human anti-TNF mAb from Knoll Pharmaceuticals) for reducing the inflammation of neuronal tissue or the neuromuscular junction of said human, or for modulating the immune response affecting neuronal tissue or the neuromuscular junction of said human; and
   b) administering a therapeutically effective dosage level to said human of an antiretroviral agent or agents for reducing the inflammation of neuronal tissue or the neuromuscular junction of said human, or for modulating the immune response affecting neuronal tissue or the neuromuscular junction of said human.

50. A method for inhibiting the action of TNF in accordance with claim 49, wherein the step of administering said TNF antagonist in the form of etanercept is performed subcutaneously in said human wherein said dosage level is in the range of 5 mg to 50 mg for acute or chronic regimens.

51. A method for inhibiting the action of TNF in accordance with claim 49, wherein the step of administering said TNF antagonist in the form of D2E7 is performed subcutaneously in said human wherein said dosage level is in the range of 20 mg to 100 mg for acute or chronic regimens.

52. A method for inhibiting the action of TNF in accordance with claim 49, wherein the step of administering said TNF antagonist in the form of infliximab is performed subcutaneously in said human wherein said dosage level is a therapeutically effective amount.

53. A method for inhibiting the action of TNF in accordance with claim 49, wherein the step of administering said TNF antagonist in the form of infliximab is performed intravenously in said human wherein said dosage level is in the range of 2.5 mg/kg to 20 mg/kg.

54. A method for inhibiting the action of TNF in accordance with claim 49, wherein the step of administering said TNF antagonist in the form of etanercept is performed intrathecally in said human wherein said dosage level is in the range of 0.1 mg to 25 mg administered from once a day to once every 3 months.

55. A method for inhibiting the action of TNF in accordance with claim 49, wherein the step of administering said TNF antagonist in the form of infliximab is performed intrathecally in said human wherein said dosage level is in the range of 0.1 mg/kg to 5 mg/kg administered from once a week to once every 3 months.

56. A method for inhibiting the action of TNF in accordance with claim 49, wherein the step of administering said TNF antagonist in the form of D2E7 is performed intrathecally in said human wherein said dosage level is in the range of 0.1 mg to 25 mg administered once a week to once every 3 months.

57. A method for inhibiting the action of TNF in accordance with claim 49, wherein the step of administering said TNF antagonist is performed intravenously in said human wherein said dosage level is a therapeutically effective amount.

58. A method for inhibiting the action of TNF in accordance with claim 49, wherein the step of administering said TNF antagonist is performed subcutaneously in said human wherein said dosage level is a therapeutically effective amount.

59. A method for inhibiting the action of TNF in accordance with claim 49, wherein the step of administering said TNF antagonist in the form of etanercept is performed intracerebroventricularly in said human wherein said dosage level is in the range of 0.1 mg to 25 mg administered once a day to once a month.

60. A method for inhibiting the action of TNF in accordance with claim 49, wherein the step of administering said TNF antagonist in the form of infliximab is performed intracerebroventricularly in said human wherein said dosage level is in the range of 0.1 mg/kg to 5 mg/kg administered once a week to once every 3 months.

61. A method for inhibiting the action of TNF in accordance with claim 49, wherein the step of administering said TNF antagonist in the form of D2E7 is performed intracerebroventricularly in said human wherein said dosage level is in the range of 0.1 mg to 25 mg administered once a week to once every 3 months.

62. A method for inhibiting the action of TNF in accordance with claim 49, wherein the step of administering said dosage level is for treating HIV Dementia, HIV-associated Myelopathy, or HIV-associated Peripheral Neuropathy.

63. A method for inhibiting the action of TNF in accordance with claim 49, wherein said antiretroviral agent or agents are selected from the group consisting of Stavudine, Lamivudine, Indinavir, Ritonavir, Nelfinavir, Saquinavir, Zidovudine, Didanosine, Delavirdine, Nevirapine, Amprenavir, and Efavirenz.

64. A method for inhibiting the action of TNF for the prevention of Postherpetic Neuralgia in a human by administering a TNF antagonist for reducing the inflammation of neuronal tissue of said human, or for modulating the immune response affecting neuronal tissue of said human, comprising the steps of:
  a) administering a therapeutically effective dosage level to said human of said TNF antagonist selected from the group consisting of etanercept, infliximab, and D2E7 (a human anti-TNF mAb from Knoll Pharmaceuticals) for reducing the inflammation of neuronal tissue of said human, or for modulating the immune response affecting neuronal tissue of said human; and
  b) administering a therapeutically effective dosage level to said human of an antiviral agent selected from the group consisting of Acyclovir, Valaciclovir, and Famciclovir for reducing the inflammation of neuronal tissue of said human, or for modulating the immune response affecting neuronal tissue of said human.

65. A method for inhibiting the action of TNF in accordance with claim 64, wherein the step of administering said TNF antagonist in the form of etanercept is performed subcutaneously in said human wherein said dosage level is in the range of 5 mg to 50 mg for acute or chronic regimens.

66. A method for inhibiting the action of TNF in accordance with claim 64, wherein the step of administering said TNF antagonist in the form of D2E7 is performed subcutaneously in said human wherein said dosage level is in the range of 20 mg to 100 mg for acute or chronic regimens.

67. A method for inhibiting the action of TNF in accordance with claim 64, wherein the step of administering said TNF antagonist in the form of infliximab is performed subcutaneously in said human wherein said dosage level is a therapeutically effective amount.

68. A method for inhibiting the action of TNF in accordance with claim 64, wherein the step of administering said TNF antagonist in the form of infliximab is performed intravenously in said human wherein said dosage level is in the range of 2.5 mg/kg to 20 mg/kg.

69. A method for inhibiting the action of TNF in accordance with claim 64, wherein the step of administering said TNF antagonist is performed subcutaneously in said human wherein said dosage level is a therapeutically effective amount.

70. A method for inhibiting the action of TNF in accordance with claim 64, wherein the step of administering said TNF antagonist is performed intravenously in said human wherein said dosage level is a therapeutically effective amount.

71. A method for inhibiting the action of TNF in accordance with claim 64, wherein the step of administering said antiviral agent in the form of Acyclovir is performed orally in said human, wherein said dosage level is 400 mg taken 2 to 5 times per day.

72. A method for inhibiting the action of TNF in accordance with claim 64, wherein the step of administering said antiviral agent in the form of Valaciclovir is performed orally in said human, wherein said dosage level is one gram taken once or twice per day.

73. A method for inhibiting the action of TNF in accordance with claim 64, wherein the step of administering said antiviral agent in the form of Famciclovir is performed orally in said human, wherein said dosage level is 250 mg to 500 mg taken 2 to 3 times per day.

74. A method for inhibiting the action of TNF for treating neurological effects of Epilepsy in a human by administering a TNF antagonist for reducing the inflammation of neuronal tissue or the neuromuscular junction of said human, or for modulating the immune response affecting neuronal tissue or the neuromuscular junction of said human, comprising the step of:
  a) administering a therapeutically effective dosage level to said human of said TNF antagonist selected from the group consisting of etanercept, infliximab, and D2E7 (a human anti-TNF mAb from Knoll Pharmaceuticals) for reducing the inflammation of neuronal tissue or the neuromuscular junction of said human, or for modulating the immune response affecting neuronal tissue or the neuromuscular junction of said human.

75. A method for inhibiting the action of TNF in accordance with claim 74, wherein the step of administering said TNF antagonist in the form of etanercept is performed subcutaneously in said human wherein said dosage level is in the range of 5 mg to 50 mg for acute or chronic regimens.

76. A method for inhibiting the action of TNF in accordance with claim 74, wherein the step of administering said TNF antagonist in the form of D2E7 is performed subcutaneously in said human wherein said dosage level is in the range of 20 mg to 100 mg for acute or chronic regimens.

77. A method for inhibiting the action of TNF in accordance with claim 74, wherein the step of administering said TNF antagonist is performed subcutaneously in said human wherein said dosage level is a therapeutically effective amount.

78. A method for inhibiting the action of TNF in accordance with claim 74, wherein the step of administering said TNF antagonist in the form of D2E7 is performed intravenously in said human wherein said dosage level is a therapeutically effective amount.

79. A method for inhibiting the action of TNF in accordance with claim 74, wherein the step of administering said TNF antagonist in the form of infliximab is performed intravenously in said human wherein said dosage level is in the range of 2.5 mg/kg to 20 mg/kg.

80. A method for inhibiting the action of TNF in accordance with claim 74, wherein the step of administering said TNF antagonist is performed intravenously in said human wherein said dosage level is a therapeutically effective amount.

81. A method for inhibiting the action of TNF for treating neurological conditions in a human by administering a TNF antagonist for reducing the inflammation of neuronal tissue of said human, or for modulating the immune response affecting neuronal tissue of said human, comprising the steps of:
   a) administering a therapeutically effective dosage level to said human of said TNF antagonist selected from the group consisting of etanercept, infliximab, and D2E7 (a human anti-TNF mAb from Knoll Pharmaceuticals) for reducing the inflammation of neuronal tissue of said human, or for modulating the immune response affecting neuronal tissue of said human; and
   b) administering a therapeutically effective dosage level to said human of an antiviral agent selected from the group consisting of Acyclovir, Valaciclovir, and Famciclovir for reducing the inflammation of neuronal tissue of said human, or for modulating the immune response affecting neuronal tissue of said human.

82. A method for inhibiting the action of TNF in accordance with claim 81, wherein the step of administering said dosage level is for treating Multiple Sclerosis.

83. A method for inhibiting the action of TNF in accordance with claim 81, wherein the step of administering said dosage level is for treating infection caused by neurotropic viruses.

84. A method for inhibiting the action of TNF in accordance with claim 81, wherein the step of administering said dosage level is for treating or preventing neurological conditions associated with infection with members of the herpes virus family, including Herpes Simplex, Varicella, EBV and CMV.

* * * * *